United States Patent
Shibuya et al.

(10) Patent No.: US 6,861,456 B2
(45) Date of Patent: Mar. 1, 2005

(54) PHOTOSENSITIVE COMPOUND, PHOTOSENSITIVE RESIN, AND PHOTOSENSITIVE COMPOSITION

(75) Inventors: Toru Shibuya, Inba-gun (JP); Masanori Kurihara, Inba-gun (JP); Mineko Takeda, Inba-gun (JP); Kazuo Yamada, Inba-gun (JP)

(73) Assignee: Toyo Gosei Kogyo Co., Ltd., Chiba (JP)

( * ) Notice: Subject to any disclaimer, the term of this patent is extended or adjusted under 35 U.S.C. 154(b) by 109 days.

(21) Appl. No.: 10/400,844

(22) Filed: Mar. 27, 2003

(65) Prior Publication Data

US 2004/0266901 A1 Dec. 30, 2004

(30) Foreign Application Priority Data

Mar. 29, 2002 (JP) ........................................ 2002-097971

(51) Int. Cl.[7] .......................... C08F 2/46; C07C 247/00
(52) U.S. Cl. ...................... 522/173; 522/174; 522/178; 522/176; 522/150; 522/151; 522/152; 522/153; 522/134; 522/135; 522/136; 522/139; 522/140; 552/1; 552/6; 552/7; 552/8; 532/100
(58) Field of Search .......................... 522/1, 178, 174, 522/176, 150, 151, 152, 153, 134, 135, 136, 139, 140; 552/1, 6, 7, 8; 532/100

(56) References Cited

U.S. PATENT DOCUMENTS

2004/0018963 A1 * 1/2004 Hudyma et al. ............... 514/8

FOREIGN PATENT DOCUMENTS

| EP | 0189271 | 7/1986 |
|---|---|---|
| EP | 1128214 | 8/2001 |
| JP | 50027404 | 3/1975 |
| JP | 50141403 | 11/1975 |
| JP | 1580959 | 12/1980 |
| JP | 61166542 | 7/1986 |
| JP | 2204750 | 8/1990 |
| JP | 4026849 | 1/1992 |
| JP | 5011442 | 1/1993 |
| JP | 5113661 | 5/1993 |
| JP | 6239930 | 8/1994 |
| JP | 0878739 | 11/1998 |

* cited by examiner

Primary Examiner—James J. Seidleck
Assistant Examiner—Sanza L. McClendon
(74) Attorney, Agent, or Firm—Huntley & Associates, LLC

(57) ABSTRACT

The present invention provides a novel photosensitive compound having an azido group suitable for exposure to light of a short wavelength; a photosensitive resin containing the photosensitive compound; and a photosensitive composition containing the photosensitive compound or photosensitive resin. The photosensitive compound containing a photosensitive unit represented by formula (1):

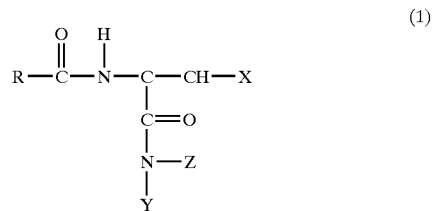

wherein R is selected from among the following groups, R:

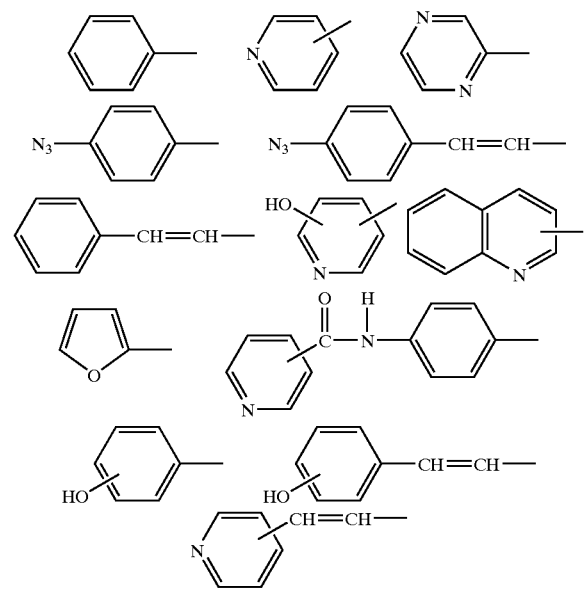

X is selected from among the following groups, X:

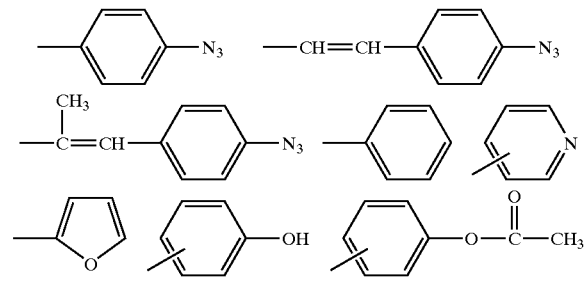

and each of Y and Z represents a hydrogen atom, an alkyl group, an acetal-group-containing alkyl group, an aryl group, an aralkyl group, or a substituent containing a base-forming nitrogen atom, wherein at least one of R and X contains an azido group.

9 Claims, No Drawings

PHOTOSENSITIVE COMPOUND, PHOTOSENSITIVE RESIN, AND PHOTOSENSITIVE COMPOSITION

BACKGROUND OF THE INVENTION

1. Field of the Invention

The present invention relates to a novel photosensitive compound, a photosensitive resin, and a photosensitive composition containing the photosensitive compound or resin, and more particularly to a novel photosensitive compound, a photosensitive resin, and a photosensitive composition containing the photosensitive compound or resin, having a wide range of utility including, for example, cathode-ray tubes and other display tubes, screen printing, immobilized enzymes, PS (presensitized) plates, etching resists, color proofs, and sandblasting resists.

2. Description of the Related Art

Conventionally, an enormous variety of photosensitive compositions have is been developed. Among them, Japanese Patent Application Laid-Open (kokai) No. 61-166542 discloses a photo-patterning resist employed for exposure at a long wavelength of 436 nm and containing an alkali-soluble polymer and an azlactone compound having an azido group.

However, the above azlactone compound fails to meet increasing demand for shorter wavelength of exposure light source employed in recent microphotolithographic techniques.

SUMMARY OF THE INVENTION

In view of the foregoing, an object of the present invention is to provide a novel photosensitive compound having an azido group suitable for exposure to light of a short wavelength. Another object of the invention is to provide a photosensitive resin containing the photosensitive compound. Still another object of the invention is to provide a photosensitive composition containing the photosensitive compound or photosensitive resin.

Accordingly, in a first aspect of the present invention, there is provided a photosensitive compound comprising a photosensitive unit represented by formula (1):

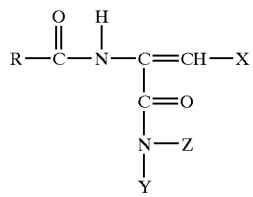

wherein R is selected from among the following groups,

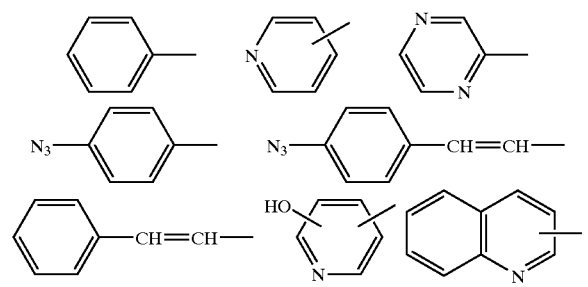

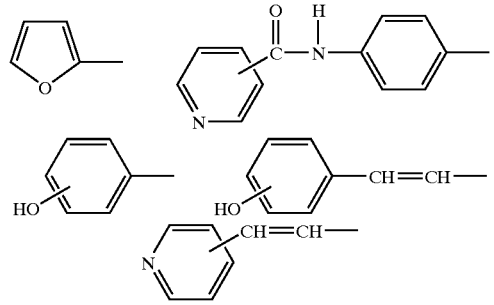

X is selected from among the following groups,

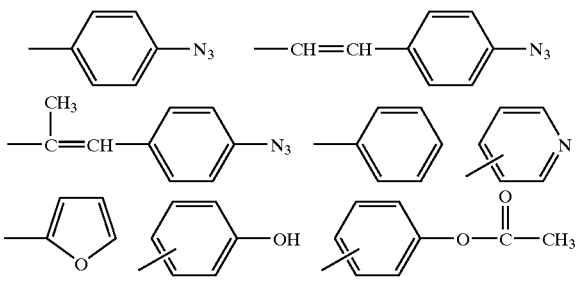

and each of Y and Z represents a hydrogen atom, an alkyl group, an acetal-group-containing alkyl group, an aryl group, an aralkyl group, or a substituent containing a base-forming nitrogen atom, wherein at least one of R and X contains an azido group.

In the photosensitive compound of the first aspect, Y may be selected from among a hydrogen atom, a methyl group, and a benzyl group, and Z may be represented by the following formula (2):

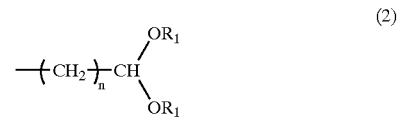

wherein $R_1$ is a C1 to C6 alkyl group, and n is 1, 2, or 3.

The photosensitive compound may contain at least two photosensitive units represented by formula (1), the units being bonded to one another by the mediation of Z.

In any one of the aforementioned photosensitive compounds, the photosensitive unit may show its absorption maximum wavelength in a range of 250 nm to 400 nm.

In a second aspect of the present invention, there is provided a photosensitive resin produced through acetalization of a saponified poly(vinyl acetate) with a photosensitive compound comprising a photosensitive unit represented by formula (1):

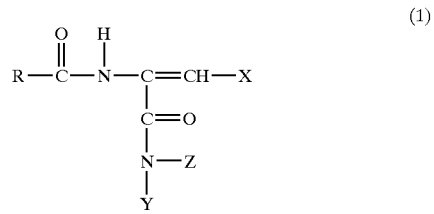

wherein R is selected from among the following groups,

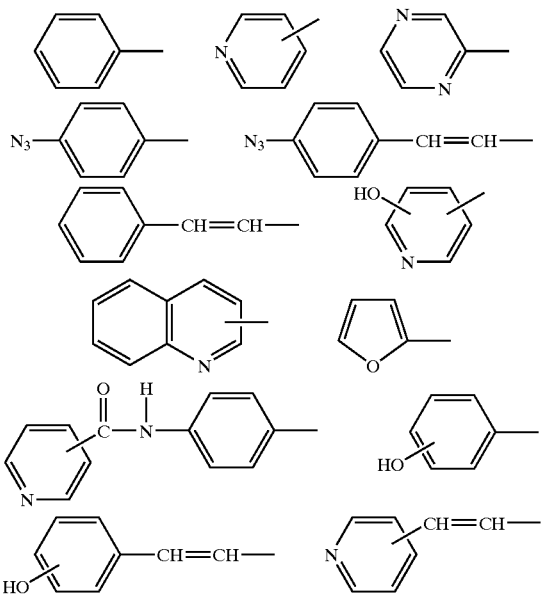

X is selected from among the following groups,

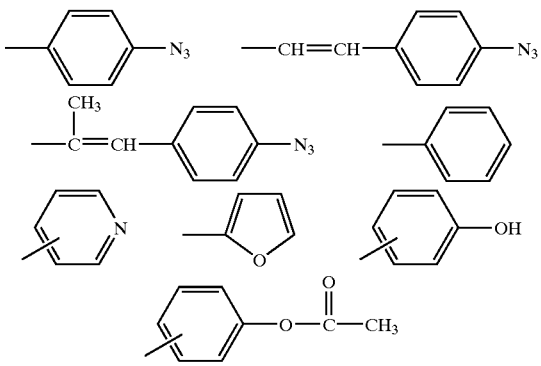

Y is selected from among a hydrogen atom, an alkyl group, and a benzyl group, and Z is a group represented by formula (2):

Z:

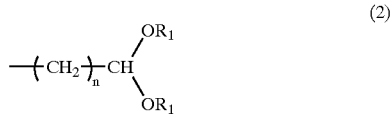

(2)

wherein $R_1$ represents a C1 to C6 alkyl group, and n is 1, 2, or 3, wherein at least one of R and X contains an azido group.

In the photosensitive resin of the second aspect, the saponified poly(vinyl acetate) may be acetalized to a percent acetalization of 0.2 to 10 mol %.

In any one of the photosensitive resins of the second aspect, the photosensitive unit may show its absorption maximum wavelength in a range of 250 nm to 400 nm.

In a third aspect of the present invention, there is provided a photosensitive composition comprising any one of the aforementioned photosensitive compounds.

In a fourth aspect of the present invention, there is provided a photosensitive composition comprising any one of the aforementioned photosensitive resins.

According to the present invention, there can be provided a novel azido-group-containing photosensitive compound which is suited for exposure to light of a short wavelength and which can be modified for adaptation to a variety of uses; a photosensitive resin containing the photosensitive compound; and a photosensitive composition containing the photosensitive compound or resin.

DETAILED DESCRIPTION OF PREFERRED EMBODIMENTS

The present invention will next be described in more detail.

The photosensitive compound per se of the present invention may be composed of a novel photosensitive unit represented by the aforementioned formula (1), or alternatively, the photosensitive compound may be a compound containing the photosensitive unit. In the latter case, the photosensitive unit should be construed to encompass the photosensitive unit of formula (1) and a moiety derived from the unit. In other words, the photosensitive compound may be a photosensitive unit represented by formula (1); a photosensitive compound containing the photosensitive unit as a portion thereof; or a photosensitive compound to which at least two photosensitive units represented by formula (1) are bonded.

At least one of R and X contained in the photosensitive unit represented by formula (1) contains an azido group. Namely, a photosensitive unit in which R contains an azido group and X contains no azido group; one in which R contains no azido group and X contains an azido group; and one in which both R and X contain an azido group all fall within the scope of the photosensitive unit represented by formula As described above, each of substituents Y and Z represents a hydrogen atom, an alkyl group, an acetal-group-containing alkyl group, an aryl group, an aralkyl group, or a substituent containing a base-forming nitrogen atom.

Although details will be described later, when Y or Z of the photosensitive compound of the present invention contains an acetal group, particularly when Z is an alkyl group containing an acetal group as represented by formula (2), a saponified poly(vinyl acetate) can be readily acetalized, thereby yielding a suitable photosensitive resin. In the case where Z is a group represented by formula (2), Y is preferably a hydrogen atom, a methyl group, or a benzyl group.

When Y or Z is a substituent containing a base-forming nitrogen atom, a composition containing polyhydroxystyrene in combination with the photosensitive compound of the present invention can be patterned through photolithography. Such a composition can be employed as an alkali-developable photosensitive composition.

The photosensitive compound of the present invention may have a variety of chemical structure. The following Tables 1 and 2 show compounds A-1 to A-16 with their substituents R, X, Y, and Z, as examples of photosensitive compounds, wherein Z is an acetal-group-containing alkyl group. As shown in Tables 1 and 2, X in compound A-1 to A-5 has an azido group, and R and X in compound A-6 have an azido group.

TABLE 1

| | R | X | Y | Z |
|---|---|---|---|---|
| A-1 | phenyl | 4-azidophenyl | H | —(CH$_2$)$_3$—CH(OCH$_3$)$_2$ |
| A-2 | phenyl | 4-azidophenyl | H | —CH$_2$—CH(OCH$_3$)$_2$ |
| A-3 | pyridin-3-yl | 4-azidophenyl | H | —(CH$_2$)$_3$—CH(OCH$_3$)$_2$ |
| A-4 | pyridin-4-yl | 4-azidophenyl | H | —CH$_2$—CH(OCH$_3$)$_2$ |
| A-5 | PhCH=CH— | 4-azidophenyl | H | —(CH$_2$)$_3$—CH(OCH$_3$)$_2$ |
| A-6 | 4-azidophenyl | 4-azidophenyl | H | —(CH$_2$)$_3$—CH(OCH$_3$)$_2$ |
| A-7 | 4-azidophenyl | pyridin-3-yl | H | —(CH$_2$)$_3$—CH(OCH$_3$)$_2$ |
| A-8 | 4-azidophenyl-CH=CH— | pyridin-3-yl | H | —(CH$_2$)$_3$—CH(OCH$_3$)$_2$ |
| A-9 | phenyl | (CH$_3$)$_2$C=CH—C$_6$H$_4$—N$_3$ | H | —(CH$_2$)$_3$—CH(OCH$_3$)$_2$ |
| A-10 | pyridin-3-yl | (CH$_3$)$_2$C=CH—C$_6$H$_4$—N$_3$ | H | —(CH$_2$)$_3$—CH(OCH$_3$)$_2$ |

TABLE 2

| | R | X | Y | Z |
|---|---|---|---|---|
| A-11 | phenyl | 4-azidophenyl | —CH$_2$—C$_6$H$_5$ | —(CH$_2$)$_3$—CH(OCH$_3$)$_2$ |
| A-12 | pyridin-3-yl | 4-azidophenyl | —CH$_2$—C$_6$H$_5$ | —(CH$_2$)$_3$—CH(OCH$_3$)$_2$ |

TABLE 2-continued

| | R | X | Y | Z |
|---|---|---|---|---|
| A-13 | 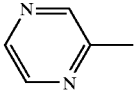 |  | —CH$_2$—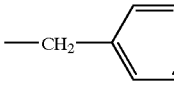 | —(CH$_2$)$_3$—CH(OCH$_3$)$_2$ |
| A-14 | 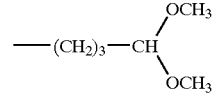 | 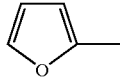 | H | —(CH$_2$)$_3$—CH(OCH$_3$)$_2$ |
| A-15 | 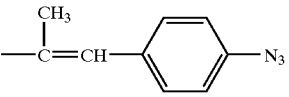 | 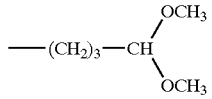 | H | —(CH$_2$)$_3$—CH(OCH$_3$)$_2$ |
| A-16 | 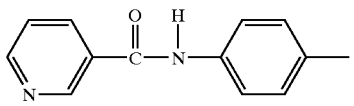 | 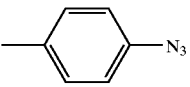 | H | —(CH$_2$)$_3$—CH(OCH$_3$)$_2$ |

Table 3 shows examples of photosensitive compounds having as Z a ing a base-forming nitrogen atom (compounds B-1 to B-4).

TABLE 3

| | R | X | Y | Z |
|---|---|---|---|---|
| B-1 | 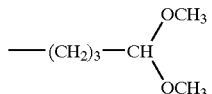 | 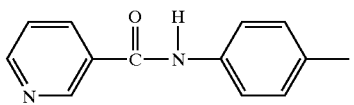 | H | —CH$_2$—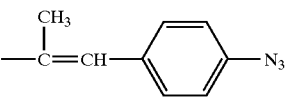 |
| B-2 | 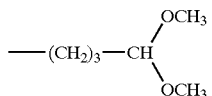 | 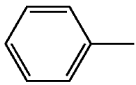 | H | —(CH$_2$)$_3$—N |
| B-3 | 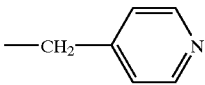 | 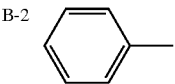 | H | —(CH$_2$)$_3$—N(CH$_3$)$_2$ |
| B-4 | 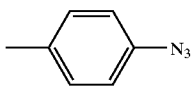 | 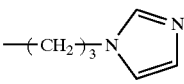 | H | —CH$_2$—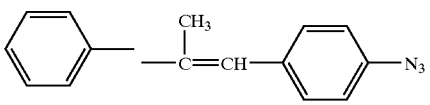 |

As mentioned above, the photosensitive compound of the present invention may contain at least two photosensitive units selected from among a variety of units represented by the aforementioned formula (1), the units being bonded to one another by the mediation of Z. In such compounds, Y is hydrogen or a substituted alkyl group.

The photosensitive unit represented by formula (1), forming the photosensitive compound of the present invention, can be synthesized in accordance with the following reaction scheme.

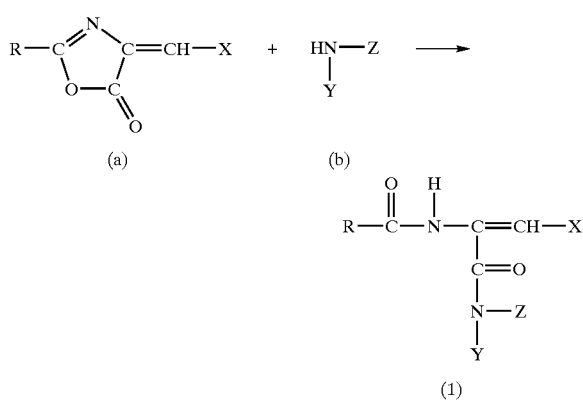

(1)

Specifically, an azlactone compound (a) containing at least one azido group in the substituent R or X is reacted with a substituted primary or secondary amine compound (b), to thereby form the photosensitive unit represented by formula (1) by opening the azlactone ring.

No particular catalyst is required for the above reaction, and the azido-group-containing azlactone compound is reacted with an equimol or slightly excessive amount of the amine compound for about 1 to about 24 hours in an appropriate solvent such as THF, acetonitrile, IPA, or DMF, to thereby yield the photosensitive unit.

When the azlactone ring of the azido-group-containing azlactone compound (a) is opened through the reaction, the ring-opened compound shows its absorption at 400 nm or shorter wavelength: i.e., the thus-formed photosensitive unit (1) of the present invention shows its absorption maximum wavelength in a range of 250 nm to 400 nm.

No particular limitation is imposed on the species of the azido-group-containing azlactone compound (a), and examples include such azlactone compounds as disclosed in Japanese Patent Application Laid-Open (koaki) No. 61-166542. The azido-group-containing azlactone compound (a) can be synthesized through, for example, condensation of an aldehyde compound or an aromatic aldehyde containing an azido group with hippuric acid (i.e., N-benzoylglycine), azidobenzoylglycine, azidocinnamoylglycine, nicotinoylglycine, etc. in the presence of acetic anhydride and sodium acetate. In the present invention, at least one species of the aldehyde and hippuric acid or similar compounds employed in the reaction contains an azido group.

Examples of azido-group-containing aldehydes for forming the azido-group-containing azlactone compound (a) include azidobenzaldehyde and azidocinnamaldehyde. The azidocinnamaldehyde compound, represented by the following formula:

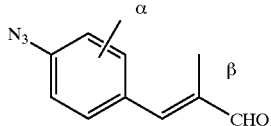

wherein $R_2$ represents hydrogen or a sulfonate salt group and $R_3$ represents a lower alkyl group, can be produced through, for example, condensation of an azidobenzaldehyde compound with a lower alkyl aldehyde. Here, a sulfonate salt group is represented by —$SO_3M$, and examples of M include lithium, sodium, potassium, ammonium, monoalkylammonium, dialkylammonium, trialkylammonium, or tetraalkylammonium. And examples of a lower alkyl group include a C1 to C4 alkyl group, preferably a linear-chain group, more preferably a methyl group or an ethyl group.

As mentioned above, the amine compound (b) to be reacted with the above azido-group-containing azlactone compound is a substituted primary amine or secondary amine. Among such amines, amine compounds having an amine moiety and an acetal skeleton are particularly useful for the synthesis of the photosensitive compound of the present invention. Specific examples include aminobutylaldehyde dimethylacetal, N-benzylaminobutylaldehyde dimethylacetal, N-methylaminobutylaldehyde dimethylacetal, aminoacetaldehyde dimethylacetal, aminoacetaldehyde diethylacetal, and 3-aminopropionaldehyde diethylacetal.

Other than the above-described amines, amines such as amines containing a base-forming nitrogen atom in a substituent thereof, bifunctional amines, polyfunctional amines, and amino-group-containing polymers may also be used.

The amino-group-containing polymers include amino-group-modified PVA, which is obtained through, for example, saponification of a copolymer of vinyl acetate and vinylacetamide or methylvinylacetamide. Copolymers of vinylacetamide or methylvinylacetamide can be produced from other vinylic monomers instead of vinyl acetate. Allylamine-vinyl acetate copolymer or a partial saponified product thereof can also be used.

Specific examples of other amine compounds to be reacted with the azido-group-containing azlactone compound include ethylenediamine, 1,3-diaminopropane, 1,4-diaminobutane, 1,6-diaminohexane, 1,7-diaminoheptane, 1,9-diaminononane, 1,12-diaminododecane, 4,4'-diaminodicyclohexylmethane, N,N-dimethyl-1,3-propanediamine (amine-113), N,N-diethylethylenediamine (amine-222), N,N-dimethylethylenediamine (amine-112), 3-(di-n-butylamino)propylamine (amine-443), 3-picolylamine, 4-picolylamine, 2-picolylamine, aminopropylmorpholine, aminoethylmorpholine, aminomethylpiperazine, aminotriazole, aminotetrazole, aminopropylimidazole, 2-methyl-1,5-pentamethylenediamine, trimethylhexane-1,6-diamine, 2,2,4-(or 2,4,4-)trimethylhexamethylenediamine, trimethylhexamethylenediamine, 5-methylnonamethylenediamine, decamethylenediamine, isophoronediamine, bis(4-aminocyclohexyl)methane, bis(3-methyl-4-aminocyclohexyl)methane, bis(3-methyl-4-amino-5-ethylcyclohexyl)methane, 1,2-bis(4-aminocyclohexyl)ethane, 2,2'-bis(4-aminocyclohexyl) propane, 2,2'-bis(3-methyl-4-aminocyclohexyl)propane, methylamine, dimethylamine, ethylamine, diethylamine, propylamine, dipropylamine, isopropylamine, diisopropylamine, butylamine, dibutylamine, isobutylamine, diisobutylamine, hexylamine, cyclohexylamine, 2-(cyclohexaneamino)sulfonic acid, octylamine, decylamine, dodecylamine, hexadecylamine, octadecylamine, propargylamine, allylamine, diglycolamine, diethylenetriamine, triethylenetetramine, tetraethylenepentamine, 1-(2-aminoethyl)piperazine, N-(2-aminoethyl)-1,3-propanediamine, 4-(aminomethyl) piperidine, 1,2-diaminopropane, 3,3'-diaminodipropylamine, 1,6-hexanediamine, 1,8-diaminooctane, 1,10-diaminodecane, 1,2-diaminocyclohexane, JEFFAMINE C-346 (trade name, product of Huntsman Corporation), JEFFAMINE D-230, JEFFAMINE D400, JEFFAMINE D-2000, JEFFAMINE D-4000, JEFFAMINE DU-700, JEFFAMINE ED-600, JEFFAMINE ED-900, JEFFAMINE ED-2001, JEFFAMINE ED-4000, JEFFAMINE ED-6000, JEFFAMINE EDR-148, JEFFAMINE T403, JEFFAMINE T-3000, JEFFAMINE T-5000, hexamethylene-bis-triacetonediamine, 2-(2-aminoethoxy)ethanol, 2-(2-aminoethylamino)ethanol, 2-(2- aminoethylamino)isopropanol, N-aminoethylisopropanolamine, 2-amino-2-ethyl-1,3-propanediol, 1-amino4-(2-hydroxyethyl)piperazine, 6-amino-1-hexanol, aminomethanetrimethanol, 5-amino-1-pentanol, 2-amino-1-pentanol, 2-aminophenol, 3-aminophenol, 4-aminophenol, N-methylaminopropyltrimethoxysilane, methyl [2-(3-trimethoxysilylpropylamino)ethylamino]-3-propionate, N-(3-acryloxy-2-hydroxypropyl)-3-aminopropyltriethoxysilane, 4-aminobutyldimethylmethoxysilane, 4-aminobutyltriethoxysilane, (aminoethylaminomethyl)phenylethyltrimethoxysilane, N-(2-aminoethyl)-3-aminopropyltrimethoxysilane, N-(6-aminohexyl)aminopropyltrimethoxysilane, 3-aminopropyldimethylethoxysilane, 3-aminopropylmethyldiethoxysilane, 3-aminopropyldiisopropylethoxysilane, 3-aminopropyltriethoxysilane, 3-aminopropyltrimethoxysilane, bis(2-hydroxyethyl)-3-aminopropyltriethoxysilane, 1,4-bis[3-(trimethoxysilyl)propyl]ethylenediamine, bis[3-(triethoxysilyl)propyl]amine, trimethoxysilylpropyldiethylenetriamine, polyaminosilane analogues derived through hydrolysis and condensation of the above alkoxyaminosilanes, 1,4-bis(3-aminopropyl)piperazine, bis(6-aminohexyl)amine, N,N-bis(3-aminopropyl)methylamine, tris(2-aminoethyl)amine, amino acid compounds such as L-glutamine, N'-methyl-2,2'-diaminodiethylamine, 3,9-bis(3-aminopropyl)-2,4,8,10-tetraoxospiro[5,5]undecanepolyallylamine, polyvinylamine, polyamidine, polyethyleneimine, diaminosiloxanes (amine-modified silicones) such as BY 16-853 and BY 16-853B (trade names, products of Dow Corning Toray Silicone Co., Ltd.), chitosan, and bisaminopropylpolytetrahydrofuran compounds such as BAP-PTHF 750, BAP-PTHF 1100, and BAP-PTHF 2100 (trade names, product of BASF).

Through reaction between any of the aforementioned amine compounds and any of the azido-group-containing azlactone compounds, a photosensitive compound including the photosensitive unit of the present invention can be produced. As mentioned above, since there are a variety of amine compounds and azido-group-containing azlactone compounds, azido-group-containing photosensitive compounds suitable for a variety of uses can be readily produced through the reaction.

For example, when an amine compound of two or more functionalities is reacted with an azido-group-containing azlactone compound, a polyfunctional, azido-group-containing compound can be readily prepared. The polyfunctional, azido-group-containing compound falling within the scope of the present invention can be photocrosslinked to a conventional polymer such as polyvinylpyrrolidone, polyvinylphenol, or phenol novolak resin.

The photosensitive compound of the present invention acetalizes a saponified poly(vinyl acetate), to thereby produce a photosensitive resin.

More specifically, the photosensitive compound of the present invention which is produced from an amine compound having a specific substituent, inter alia, an acetal group as Z and an azido-group-containing azlactone compound can acetalize a saponified poly(vinyl acetate) under acidic conditions, attaining high yield with respect to the acetal product. The thus-obtained photosensitive resin has a structural unit represented by, for example, the following formula (3).

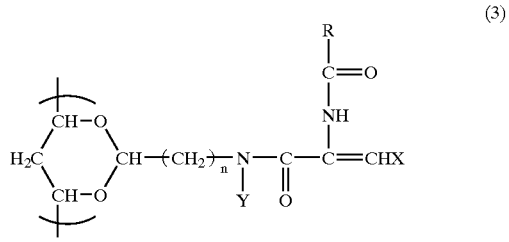

The photosensitive resin of the present invention possesses excellent photo-curability, even when the resin contains a photosensitive unit in an amount of only some mol %. Particularly, a photosensitive resin obtained through acetalization of a saponified poly(vinyl acetate) with the photosensitive compound in a percent acetalization of 0.2 to 10 mol % exhibits excellent performance.

The term "saponified poly(vinyl acetate)" which is employed in the present invention refers to poly(vinyl alcohol) or a water-soluble copolymer of vinyl alcohol and another vinyl compound. The "saponified poly(vinyl acetate)" may also include a saponified poly(vinyl acetate) modified with a hydrophilic group, a hydrophobic group, an anion, a cation, an amido group, or a reactive group such as an acetoacetyl group.

Preferably, the poly(vinyl alcohol) used in the present invention has an average polymerization degree of 200–5,000 and a saponification degree of 60–100%, for example. When the average polymerization degree is less than 200, obtaining the sufficient sensitivity is difficult, whereas when it is in excess of 5,000, the viscosity of a solution of the photosensitive resin increases, often disadvantageously resulting in poor coating characteristics. Furthermore, when the concentration is decreased in order to reduce the viscosity, obtaining the desired coating film thickness is difficult. When the saponification degree is less than 60%, obtaining sufficient water-solubility and water-developability is difficult.

The water-soluble copolymer of vinyl alcohol and another vinyl compound which may be used has an average polymerization degree of 200–5,000, for example. Examples of the vinyl monomers to be copolymerized with vinyl alcohol include N-vinylpyrrolidone and acrylamide.

When such saponified poly(vinyl acetate) are reacted with the photosensitive compound represented by the above-described formula (1) in the presence of an acid catalyst to thereby obtain the photosensitive resin, an aldehyde or a ketone may simultaneously be reacted. Examples of aldehydes include aliphatic aldehydes or their acetals such as formaldehyde, acetaldehyde, propionaldehyde, butylaldehyde, and crotonaldehyde; aromatic aldehydes or their acetals such as benzaldehyde sulfonate, benzaldehyde disulfonate, sodium 4-azido-2-sulfobenzaldehyde, carboxybenzaldehyde, hydroxybenzaldehyde, and a formylstyrylpyridinium salt. Examples of ketones include acetone and methyl ethyl ketone.

Acetalization may be performed in the presence of a solvent. Water or a mixture of water and an organic solvent which can be used in combination with water can be employed. Examples of the organic solvent include methanol, ethanol, isopropyl alcohol, butanol, propylene glycol monomethyl ether, and y-butyrolactone.

By incorporating the photosensitive compound or photosensitive resin according to the present invention into a photosensitive composition, a preferred photosensitive composition can be provided.

The photosensitive compound or photosensitive resin of the present invention contains a photosensitive unit showing its absorption maximum wavelength in a range of 250 nm to 400 nm. Therefore, when the photosensitive compound or photosensitive resin of the present invention is incorporated into a photosensitive composition, a photosensitive unit suitable for exposure to light of a short wavelength can be imparted to the photosensitive composition.

Specifically, the photosensitive compound is mixed with a photo-crosslinkable polymer such as polyvinylpyrrolidone or poly(vinyl phenol), thereby providing a photosensitive composition. In this case, another water-soluble polymer, additives, and another water-soluble azide compound may further be added to the composition.

Generally, the photosensitive resin of the present invention represented by, for example, formula (3) is dissolved in water or a mixture of water and organic solvent, to thereby yield a solution, if necessary followed by addition of additives or a similar substance, to thereby yield a photosensitive composition. In this case, photo-crosslinkable polymer, another water-soluble polymer, additives, and another water-soluble azide compound may also be added to the composition.

The photosensitive composition of the present invention may contain a water-soluble polymer. Examples of the polymer include a saponified poly(vinyl acetate); a polymer of natural product such as gelatin, a cellulose derivative, or casein; and a polymer or a copolymer comprising a water-soluble vinyl monomer. Examples of the water-soluble vinyl monomer include N-vinylformamide, N-vinylacetamide, vinylpyrrolidone, acrylamide, diacetoneacrylamide, N,N-dimethylacrylamide, vinylpyridine, methacrylamide, and allylthiourea.

As described above, the photosensitive resin may be used in combination with a water-soluble azide compound. Examples of the water-soluble azide compounds include 4,4'-diazidostilbene-2,2'-disulfonic acid, 4,4'-diazidobenzalacetophenone-2-sulfonic acid, 4,4'-diazidostilbene-α-carboxylic acid, and salts thereof such as alkali metal salts, ammonium salts, and organic amine salts. Further, there are preferably used water-soluble azide compounds described in Japanese Patent Publication (kokoku) No. 50-27404 and Japanese Patent Application Laid-Open (kokai) Nos. 50-141403, 2-204750, 4-26849, 5-11442, 5-113661, and 6-239930.

Additives such as ethylene glycol, sorbitol, and surfactants may optionally be added to the photosensitive resin composition used in the present invention in order to improve the coatability and moisture-retention property thereof.

A silane coupling agent which serves as an adhesion-accelerator may optionally be added to the photosensitive resin composition used in the present invention in order to improve adhesion thereof to a substrate. Examples of the adhesion-accelerators which may be used include water-soluble silane compounds such as N-β(aminoethyl)-aminopropylmethyldimethoxysilane and N—P (aminoethyl)-γ-aminopropyltrimethoxysilane.

Additives such as a preservative, a defoaming agent, and a pH-adjusting agent may optionally be added to the photosensitive resin composition used in the present invention. Hydrophobic polymer emulsions may optionally be added to the photosensitive resin composition used in the present invention in order to improve the film strength, water resistance, and adhesion to a variety of substrates. Examples of the hydrophobic emulsions include a poly(vinyl acetate) emulsion, a poly(acrylic acid) emulsion, and a urethane emulsion. A pattern formation method by use of a composition containing the hydrophobic polymer emulsion is suitably employed for a screen printing plate, for example.

Further, colorants such as a pigment or a dye may be added to the photosensitive resin composition used in the present invention in order to prevent halation induced by exposure or to obtain a colored image.

In particular, the colored image obtained through dispersing a pigment in the photosensitive resin composition used in the present invention may be applied to a color filter for a liquid crystal display, for a color cathode-ray tube, and for a plasma display; a color proof for printing; a secondary original image for printing; etc.

EXAMPLES

The present invention will next be described in detail by way of examples, which should not be construed as limiting the invention thereto.

Synthesis Example 1

Synthesis of compound A-1

Hippuric acid (17.9 g), azidobenzaldehyde (15 g), acetic anhydride (20 g), sodium acetate (1.0 g), toluene (25 g), and acetonitrile (20 g) were mixed together, and the mixture was heated at 70° C. for six hours, and subsequently allowed to cool. Sixteen hours after the start of cooling, the mixture was filtered at room temperature. The solid remaining on the filter was washed with cold methanol (40 g) and dried under reduced pressure, to thereby yield 17 g of an azlactone compound having an azido group; i.e., 4-((4-azidophenyl) methylene)-2-phenyl-1,3-oxazolin-5-one. The azlactone compound was found to show its absorption maximum wavelength at 390 nm.

The thus-obtained azlactone compound was dispersed in THF (150 g), and aminobutylaldehyde dimethylacetal (8.6 g) was gradually added to the dispersion at 5 to 101° C. Two hours after addition, the reaction mixture showed a new absorption at 310 nm, whereas the absorption at 390 nm disappeared. Subsequently, water (500 g) was added to the reaction mixture, followed by stirring for two hours. The thus-formed precipitates were collected through filtration, to thereby yield 1 μg of 3-(4-azidophenyl)-N-(4,4-dimethoxybutyl)-2-(phenylcarbonylamino)-prop-2-enamide (compound A-1). The obtained compound was identified on the basis of the $^1$H-NMR measurements shown in Table 4.

TABLE 4

| ppm | Type | H | J value |
|---|---|---|---|
| 8.67 | s | 1 H | |
| 7.86 | d | 2 H | 7.6 |
| 7.52 | t | 1 H | 7.2 |
| 7.41 | t | 2 H | 8 |
| 7.34 | d | 2 H | 8.4 |
| 7.05 | s-like | 1 H | |
| 6.89 | dt | 2 H | 8.4 |
| 6.75 | s | 1 H | 2.8 |
| 4.33 | t | 1 H | 5.2 |
| 3.29 | s | 6 H | |
| 3.21 | AB-q | 2 H | 6.8, 12.6 |
| 1.61–1.52 | m | 4 H | |

Example 1

Synthesis of photosensitive PVA from compound A-1

Poly(vinyl alcohol) (EG-30, product of The Nippon Synthetic Chemical Ind. Co., Ltd.) (100 g) was dissolved in water (700 g) methanol (200 g). Compound A-1 (10 g) synthesized in Synthesis Example 1 and phosphoric acid (3 g) were added to the solution, and the resultant mixture was allowed to react at 60° C. for 24 hours. Percent acetalization was found to be 97%. Subsequently, the phosphoric acid was removed through ion exchange, thereby yielding a photosensitive liquid containing PVA to which photosensitive groups had been introduced at 0.8 mol % (based on PVA). The photosensitive liquid was diluted with water/methanol (70/30 (wt.)) to a concentration of 5.5 wt. %, and the thus-diluted photosensitive liquid was applied to a glass plate so as to form a photosensitive film (thickness: 1.0 μm). The film was irradiated with UV rays for 10 seconds at an irradiance of 5 mW/cm$^2$ (light source: ultrahigh pressure mercury lamp, by use of an irradiance meter (UV-35, product of ORC)). After the exposure, the photosensitive film was developed with water, confirming that a 50 μm-wide line was clearly developed without development failure.

Synthesis Example 2

Synthesis of compound A-2

The procedure of Synthesis Example 1 was repeated, except that aminoacetaldehyde dimethylacetal (8.6 g) was used instead of aminobutylaldehyde dimethylacetal, to thereby yield 17 g of 3-(4-azidophenyl)-N-(2,2-dimethoxyethyl)-2-(phenylcarbonylamino)-prop-2-enamide (compound A-2). The azlactone compound was found to show its absorption maximum wavelength at 310 mm.

Synthesis Example 3

Synthesis of compound A-3

Nicotinoylglycine (18.0 g), azidobenzaldehyde (15 g), acetic anhydride (30 g), sodium acetate (1.0 g), and cyclohexane (30 g) were mixed together, and the mixture was heated at 70° C. for six hours, and subsequently allowed to cool. Sixteen hours after the start of cooling, IPA (30 g) was added to the mixture, and the resultant mixture was filtered at room temperature. The solid remaining on the filter was washed with cold methanol (30 g) and dried under reduced pressure, to thereby yield 10 g of an azlactone compound having an azido group; i.e., 4-((4-azidophenyl)methylene)-2-(3-pyridyl)-1,3-oxazolin-5-one. The azlactone compound was found to show its absorption maximum wavelength at 390 nm.

The thus-obtained azlactone compound was dispersed in IPA (55 g), and aminobutylaldehyde dimethylacetal (4.6 g) was gradually added to the dispersion at 5 to 10° C. Two hours after addition, the reaction mixture showed a new absorption at 310 nm, whereas the absorption at 390 nm disappeared. Subsequently, water (500 g) was added to the reaction mixture, and the pH of the mixture was adjusted to 8.0 through addition of aqueous ammonia, followed by stirring at 5° C. for two hours. The thus-formed precipitates were collected through filtration, to thereby yield 6 g of 3-(4-azidophenyl)-N-(4,4-dimethoxybutyl)-2-((3-pyridyl) carbonylamino)-prop-2-enamide (compound A-3).

Example 2

Synthesis of photosensitive PVA from compound A-3

Poly(vinyl alcohol) (EG-30, product of The Nippon Synthetic Chemical Ind. Co., Ltd.) (100 g) was dissolved in water (900 g). Compound A-3 (10 g) synthesized in Synthesis Example 3 and phosphoric acid (3 g) were added to the solution, and the mixture was allowed to react at 60° C. for 24 hours. Percent acetalization was found to be 97%. Subsequently, the phosphoric acid was removed through ion exchange, thereby yielding a photosensitive liquid containing PVA to which photosensitive groups had been introduced at 0.8 mol % (based on PVA). The photosensitive liquid was diluted with water to a concentration of 5.5%, and the thus-diluted photosensitive liquid was applied to a glass plate so as to form a photosensitive film (thickness: 1.0 μm). The film was irradiated with UV rays for 10 seconds at an irradiance of 5 mW/cm$^2$ (light source: ultrahigh pressure mercury lamp, by use of an irradiance meter (UV-35, product of ORC)). After the exposure, the photosensitive film was developed with water, confirming that a 50 μm-wide line was clearly developed without development failure.

Synthesis Example 4

Synthesis of compound A-7

Azidobenzoylglycine (10.0 g), 3-pyridinealdehyde (5 g), acetic anhydride (12 g), sodium acetate (1.0 g), and cyclohexane (12 g) were mixed together, and the mixture was heated at 70° C. for six hours, and subsequently allowed to cool. And IPA (20 g) was added to the mixture. After sixteen hours, the resultant mixture was filtered at room temperature. The solid remaining on the filter was washed with cold methanol (40 g) and dried under reduced pressure, to thereby yield 10 g of an azlactone compound having an azido group; i.e., 2-(4-azidophenyl)4-(3-pyridylmethylene)-1,3-oxazolin-5-one. The azlactone compound was found to show its absorption maximum wavelength at 372.4 nm.

The thus-obtained azlactone compound was dispersed in methanol (100 g), and aminobutylaldehyde dimethylacetal (6.0 g) was gradually added to the dispersion at 5 to 10° C. Two hours after addition, the reaction mixture showed a new absorption at 271.6 nm, whereas the absorption at 372.4 nm disappeared. Subsequently, water (150 g) and aqueous ammonia (2 cc) were added to the reaction mixture, followed by stirring for two hours. The thus-formed precipitates were collected through filtration, to thereby yield 6 g of 2-((4-azidophenyl)carbonylamino)-N-(4,4-dimethoxybutyl)-3-(3-pyridyl)prop-2-enamide (compound A-7).

Synthesis Example 5

Synthesis of compound A-8

Azidocinnamoylglycine (9 g), 3-pyridinealdehyde (4 g), acetic anhydride (12 g), sodium acetate (0.6 g), and cyclohexane (35 g) were mixed together, and the mixture was heated at 70° C. for six hours, and subsequently allowed to cool. And IPA (30 g) was added to the mixture. After sixteen hours, the resultant mixture was filtered at room temperature. The solid remaining on the filter was washed with cold methanol (30 g) and dried under reduced pressure, to thereby yield 7 g of an azlactone compound having an azido group; i.e., 2-(2-(4-azidophenyl)vinyl)-4-(3-pyridylmethylene)-1, 3-oxazolin-5-one. The azlactone compound was found to show its absorption maximum wavelength at 390 nm.

The thus-obtained azlactone compound was dispersed in THF (70 g), and aminobutylaldehyde dimethylacetal (3.0 g) was gradually added to the dispersion at 5 to 10° C. Two hours after addition, the reaction mixture showed a new absorption at 316 nm, whereas the absorption at 390 mm disappeared. Subsequently, water (200 g) and aqueous ammonia (2 cc) were added to the reaction mixture, followed by stirring for two hours. The thus-formed precipitates were collected through filtration, to thereby yield 3.5 g of 2-(3-(4-azidophenyl)prop-2-enoylamino)-N-(4,4-dimethoxybutyl)-3-(3-pyridyl)prop-2-enamide (compound A-8). The obtained compound was identified on the basis of the $^1$H-NMR measurements shown in Table 5.

TABLE 5

| ppm | Type | H | J value |
|---|---|---|---|
| 8.97 | s | 1 H | |
| 8.55 | s | 1 H | |
| 8.42 | d | 1 H | 4 |
| 7.73 | d | 1 J | 8 |
| 7.51 | d | 1 H | 15.6 |
| 7.39 | d | 2 H | 8.8 |
| 7.24 | dd | 1 H | 4.8, 8.0 |
| 7.08 | t | 1 H | 5.2 |
| 6.96 | d | 2 H | 8.4 |
| 6.60 | s | 1 H | |
| 6.51 | d | 1 H | 15.6 |
| 4.36 | t | 1 H | 4.8 |
| 3.31 | s | 6 H | |
| 3.31–3.28 | m | 2 H | |
| 1.66–1.59 | m | 4 H | |

Example 3

Synthesis of photosensitive PVA from compound A-8

Poly(vinyl alcohol) (EG-30, product of The Nippon Synthetic Chemical Ind. Co., Ltd.) (50 g) was dissolved in water (450 g). Compound A-8 (3.5 g) synthesized in Synthesis Example 5 and phosphoric acid (1.5 g) were added to the solution, and the resultant mixture was allowed to react at 60° C. for 24 hours. Percent acetalization was found to be 97%. Subsequently, the phosphoric acid was removed through ion exchange, thereby yielding a photosensitive liquid containing PVA to which photosensitive groups had been introduced at 0.8 mol % (based on PVA). The photosensitive liquid was diluted with water to a concentration of 5.5%, and the thus-diluted photosensitive liquid was applied to a glass plate so as to form a photosensitive film (thickness: 1.0 µm). The film was irradiated with UV rays for 3' seconds at an irradiance of 5 mW/cm$^2$ (light source: ultrahigh pressure mercury lamp, by use of an irradiance meter (UV-35, product of ORC)). After the exposure, the photosensitive film was developed with water, confirming that a 50 µm-wide line was clearly developed without development failure.

Synthesis Example 6

Synthesis of compound A-9

4-Azidobenzaldehyde (29.42 g, 0.2 mol) and propionaldehyde (12.22 g, 0.2 mol) were dissolved in isopropyl alcohol (100 g)-water (50 g). Sodium hydroxide (2 g) dissolved in pure water (20 g) was added to the solution, and the mixture was stirred for two hours, while the reaction mixture was cooled in an ice bath. Propionaldehyde (12.22 g, 0.2 mol) was added again to the mixture, and the resultant mixture was further stirred for three hours. The formed precipitates were collected through filtration and dried, to thereby yield 23.14 g of p-azido-2-methylcinnamaldehyde (α-methylazidocinnamaldehyde) as yellow crystals (yield: 62%).

Hippuric acid (17.9 g), the above-produced α-methylazidocinnamaldehyde (18.7 g), acetic anhydride (30 g), sodium acetate (1.0 g), toluene (25 g), and acetonitrile (20 g) were mixed together, and the mixture was heated at 60° C. for 24 hours, and subsequently allowed to cool. Sixteen hours after the start of cooling, the mixture was filtered at room temperature. The solid remaining on the filter was washed with cold methanol (40 g) and dried under reduced pressure, to thereby yield 23 g of an azlactone compound having an azido group; i.e., 4-(4-azido-β-methyl-cinnamylidene)-2-phenyl-2-oxazolin-5-one. The azlactone compound was found to show its absorption maximum wavelength at 398 nm. The thus-obtained azlactone compound was dispersed in THF (230 g), and aminobutylaldehyde dimethylacetal (10 g) was gradually added to the dispersion at 5 to 10° C. Two hours after addition, the reaction mixture showed a new absorption at 328 nm, whereas the absorption at 398 nm disappeared. Subsequently, water (345 g) was added to the reaction mixture, followed by stirring for two hours. The thus-formed precipitates were collected through filtration, to thereby yield 29 g of 5-(4-azidophenyl)-N-(4,4-dimethoxybutyl)-4-methyl-2-phenylcarbonylamino-penta-2,4-dienamide (compound A-9). The obtained compound was identified on the basis of the $^1$H-NMR measurements shown in Table 6.

TABLE 6

| ppm | Type | H | J value |
|---|---|---|---|
| 8.50 | s | 1 H | |
| 7.92 | d | 2 H | 7.2 |
| 7.52 | t | 1 H | 7.2 |
| 7.42 | t | 2 H | 8 |
| 7.21 | d | 2 H | 8.8 |
| 6.94 | d | 2 H | 8.4 |
| 6.79 | t | 1 H | 5.6 |
| 6.74 | s | 1 H | |
| 6.61 | s | 1 H | |
| 4.33 | t | 1 H | 5.2 |
| 3.31 | t | 2 H | 6.4 |
| 3.28 | s | 6 H | |
| 2.07 | s | 3 H | |
| 1.64–1.58 | m | 4 H | |

Example 4

Synthesis of photosensitive PVA from compound A-9

Poly(vinyl alcohol) (EG-05, product of The Nippon Synthetic Chemical Ind. Co., Ltd.) (100 g) was dissolved in water (630 g) methanol (270 g). Compound A-9 (7 g) synthesized in Synthesis Example 6 and phosphoric acid (3 g) were added to the solution, and the resultant mixture was allowed to react at 60° C. for 24 hours. Percent acetalization was found to be 98%. Subsequently, the phosphoric acid was removed through ion exchange, thereby yielding a photosensitive liquid containing PVA to which photosensitive groups had been introduced at 0.8 mol % (based on PVA). The photosensitive liquid was diluted with water-methanol (7:3), and the thus-prepared 8% photosensitive liquid was applied to a glass plate so as to form a photosensitive film (thickness: 1.0 µm). The film was irradiated with UV rays for 10 seconds at an irradiance of 5 mW/cm$^2$ (light source: ultrahigh pressure mercury lamp, by use of an irradiance meter (UV-35, product of ORC)). After the exposure, the photosensitive film was developed with water, confirming that a 50 µm-wide line was clearly developed without development failure.

Synthesis Example 7

Synthesis of compound A-10

Nicotinoylglycine (18 g), α-methylazidocinnamaldehyde (18.7 g, produced in Synthesis Example 6), acetic anhydride (30 g), sodium acetate (1.0 g), cyclohexane (30 g), and acetonitrile (10 g) were mixed together, and the mixture was heated at 60° C. for 24 hours, and subsequently allowed to cool. And IPA (30 g) was added to the mixture. After Sixteen hours, the mixture was filtered at room temperature. The solid remaining on the filter was washed with cold methanol (40 g) and dried under reduced pressure, to thereby yield 18 g of an azlactone compound having an azido group; i.e., 4-(4-azido-p-methyl-cinnamylidene)-2-(3-pyridyl)-2-oxazolin-5-one. The azlactone compound was found to show its absorption maximum wavelength at 401 nm.

The thus-obtained azlactone compound was dispersed in THF (230 g), and aminobutylaldehyde dimethylacetal (10 g) was gradually added to the dispersion at 5 to 10° C. Two hours after addition, the reaction mixture showed a new absorption at 323 nm, whereas the absorption at 401 nm disappeared. Subsequently, water (49.5 g) was added to the reaction mixture, followed by stirring for two hours. The thus-formed precipitates were collected through filtration, to thereby yield 27 g of 5-(4-azidophenyl)-N-(4,4-dimethoxybutyl)-4-methyl-2-((3-pyridyl)carbonylamino)-penta-2,4-dienamide (compound A-10).

Example 5

Synthesis of photosensitive PVA from compound A-10 Poly(vinyl alcohol) (EG-30, product of The Nippon Synthetic Chemical Ind.

Co., Ltd.) (100 g) was dissolved in water (900 g). Compound A-10 (7 g) synthesized in Synthesis Example 7 and phosphoric acid (3 g) were added to the solution, and the resultant mixture was allowed to react at 60° C. for 24 hours. Percent acetalization was found to be 98%. Subsequently, the phosphoric acid was removed through ion exchange, thereby yielding a photosensitive liquid containing PVA to which photosensitive groups had been introduced at 0.8 mol % (based on PVA). The photosensitive liquid was diluted with water, and the thus-prepared 4.8% photosensitive liquid was applied to a glass plate so as to form a photosensitive film (thickness: 1.0 µm). The film was irradiated with UV rays for 2 seconds at an irradiance of 5 mW/cm² (light source: ultrahigh pressure mercury lamp, by use of an irradiance meter (UV-35, product of ORC)). After the exposure, the photosensitive film was developed with water, confirming that a 50 µm-wide line was clearly is developed without development failure.

Synthesis Example 8

Synthesis of compound B-2

The procedure of Synthesis Example 1 was repeated to thereby yield 17 g of an azlactone compound having an azido group; i.e., 4-((4-azidophenyl)methylene)-2-phenyl-1,3-oxazolin-5-one.

The thus-obtained azlactone compound was dispersed in THF (150 g), and 1-(3-aminopropyl)imidazole (8.1 g) was gradually added to the dispersion at 5 to 10° C. Two hours after addition, the reaction mixture showed a new absorption at 310 nm, whereas the absorption at 390 nm disappeared. Subsequently, water (500 g) was added to the reaction mixture, followed by stirring for two hours. The thus-formed precipitates were collected through filtration, to thereby yield 16 g of 3-(4-azidophenyl)-N-(3-imidazoylpropyl)-2-(phenylcarbonylarino)-prop-2-enamide (compound B-2).

Example 6

Photosensitivity evaluation of a photosensitive PHS containing compound B-2

Polyhydroxystyrene(PHS) (VP 15000, product of Nippon Soda Co., Ltd.) (1 g) was dissolved in y-butyrolactone (4 g), and compound B-2 (0.25 g) prepared in Synthesis Example 8 was dissolved in the solution, to thereby prepare a photosensitive liquid. The liquid was applied to an silicon wafer so as to form a photosensitive film (thickness: 1.0 µm), followed by drying at 80° C. for five minutes. The film was irradiated with UV rays by use of a ultrahigh pressure mercury lamp at a dose of 200 mJ/cm² (irradiance: 5.0 mW/cm², by use of an irradiance meter (UV-35, product of ORC)). After the exposure, the photosensitive film was dried at 80° C. for five minutes and developed with an alkali developer (2.38% aqueous TMAH solution), thereby yielding a pattern without development failure.

As described hereinabove, according to the present invention, there can be provided an novel azido-group-containing photosensitive compound which is suited for exposure to light of a short wavelength; a photosensitive resin containing the photosensitive compound; and a photosensitive composition containing the photosensitive compound or resin. Since starting materials for producing the photosensitive compound can be selected from a variety of compounds, azido-group-containing photosensitive compounds suitable for a variety of uses can be readily produced. The photosensitive compound, from which photosensitive resins and photosensitive compositions can be produced, finds a variety of uses.

What is claimed is:

1. A photosensitive compound comprising a photosensitive unit represented by formula (1):

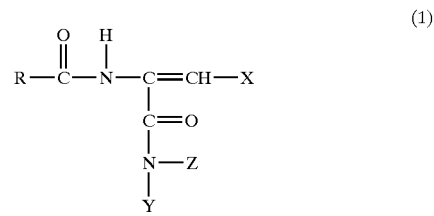

(1)

wherein R is selected from among the following groups,

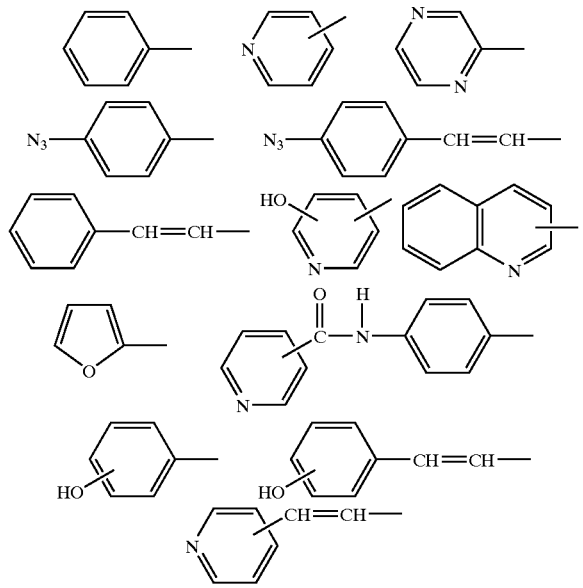

X is selected from among the following groups,

X:

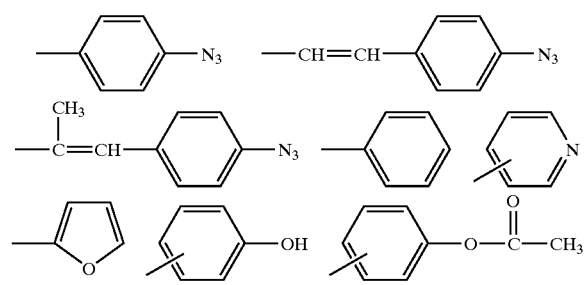

and each of Y and Z represents a hydrogen atom, an alkyl group, an acetal-group-containing alkyl group, an aryl group, an aralkyl group, or a substituent containing a base-forming nitrogen atom, wherein at least one of R and X contains an azido group.

2. A photosensitive compound according to claim 1, wherein Y is selected from among a hydrogen atom, a methyl group, and a benzyl group, and Z is represented by the following formula (2):

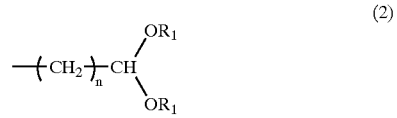

(2)

wherein $R_1$ is a C1 to C6 alkyl group, and n is 1, 2, or 3.

3. A photosensitive compound according to claim 1, which contains at least two photosensitive units represented by formula (1), the units being bonded to one another by the mediation of Z.

4. A photosensitive compound according to claim 1, wherein the photosensitive unit shows its absorption maximum wavelength in a range of 250 nm to 400 nm.

5. A photosensitive resin produced through acetalization of a saponified poly(vinyl acetate) with a photosensitive compound comprising a photosensitive unit represented by formula (1):

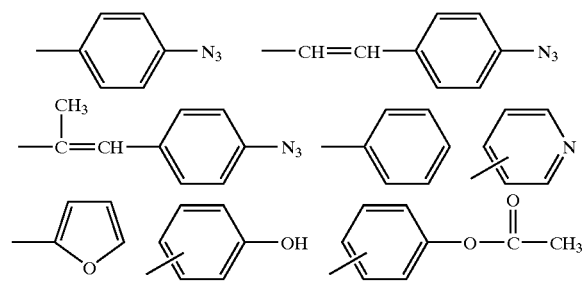

wherein R is selected from among the following groups,

R:

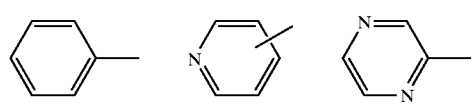

X is selected from among the following groups,

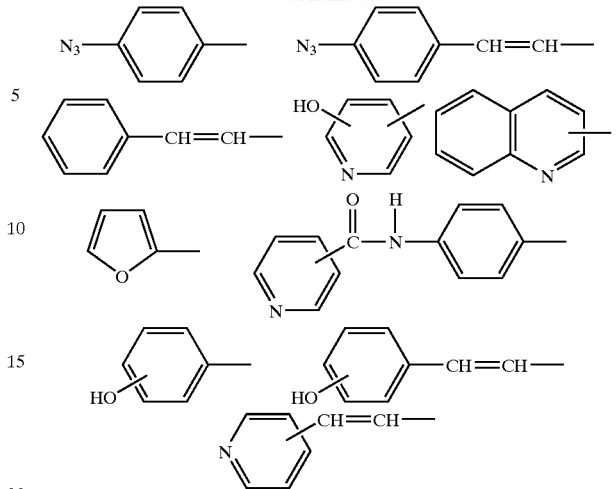

X is selected from among the following groups,

X:

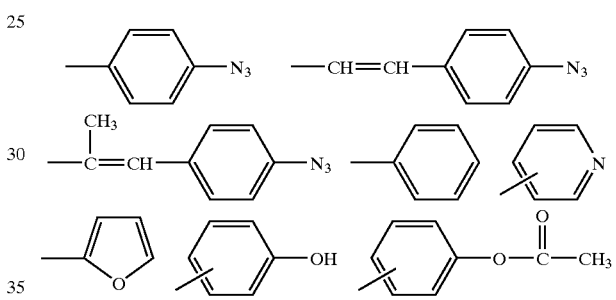

Y is selected from among a hydrogen atom, an alkyl group, and a benzyl group, and Z is a group represented by formula (2):

Z:

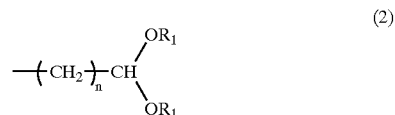

(2)

wherein $R_1$ represents a C1 to C6 alkyl group, and n is 1, 2, or 3, wherein at least one of R and X contains an azido group.

6. A photosensitive resin according to claim 5, wherein the saponified poly(vinyl acetate) is acetalized to a percent acetalization of 0.2 to 10 mol %.

7. A photosensitive resin according to claim 5, wherein the photosensitive unit shows its absorption maximum wavelength in a range of 250 nm to 400 nm.

8. A photosensitive composition comprising a photosensitive compound as recited in any one of claims 1 to 4.

9. A photosensitive composition comprising a photosensitive resin as recited in any one of claims 5 to 7.

* * * * *